US012721681B2

(12) United States Patent
Quevedo Gonzalez et al.

(10) Patent No.: US 12,721,681 B2
(45) Date of Patent: Sep. 1, 2026

(54) SYSTEM AND METHOD TO ASSESS MECHANICAL OUTCOMES FOLLOWING JOINT ARTHROPLASTY

(71) Applicant: New York Society for the Relief of the Ruptured and Crippled, maintaining the Hospital for Special Surgery, New York, NY (US)

(72) Inventors: Fernando J. Quevedo Gonzalez, Stamford, CT (US); Jonathan D. Glenday, New York, NY (US); Joseph D. Lipman, New York, NY (US); Timothy M. Wright, New York, NY (US); Jonathan M. Vigdorchik, New York, NY (US); Peter K. Sculco, New York, NY (US); David J. Mayman, New York, NY (US); Cynthia A. Kahlenberg, New York, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

(21) Appl. No.: 18/696,712

(22) PCT Filed: Sep. 28, 2022

(86) PCT No.: PCT/US2022/045117
§ 371 (c)(1),
(2) Date: Mar. 28, 2024

(87) PCT Pub. No.: WO2023/055855
PCT Pub. Date: Apr. 6, 2023

(65) Prior Publication Data

US 2024/0398480 A1 Dec. 5, 2024

Related U.S. Application Data

(60) Provisional application No. 63/249,327, filed on Sep. 28, 2021.

(51) Int. Cl.
*A61B 34/10* (2016.01)
*A61F 2/30* (2006.01)
*A61F 2/38* (2006.01)

(52) U.S. Cl.
CPC .......... *A61B 34/10* (2016.02); *A61F 2/30942* (2013.01); *A61F 2/3877* (2013.01);
(Continued)

(58) Field of Classification Search
CPC .............. A61B 34/10; A61B 2034/105; A61B 2034/104; A61B 2034/108; A61F 2/4657;
(Continued)

(56) References Cited

U.S. PATENT DOCUMENTS 8,718,748 B2 5/2014 Reinhold
8,840,527 B2 9/2014 Zhang et al.
(Continued)

FOREIGN PATENT DOCUMENTS

WO 2024238669 A2 11/2024

OTHER PUBLICATIONS

International Search Report and Written Opinion for corresponding PCT Application No. PCT/US22/45117 dated Jan. 31, 2023 (10 pages).

(Continued)

*Primary Examiner* — Igor N Borissov
(74) *Attorney, Agent, or Firm* — Leason Ellis LLP

(57) ABSTRACT

A computerized system and method to assess joint level biomechanics and fixation level biomechanics of joint arthroplasty devices. At least one computing device, con- (Continued)

figured by executing instructions stored on non-transitory processor readable media receives preoperative medical information of a person requiring joint arthroplasty. Further, the at least one computing device determines, as a function of at least some of the preoperative medical information of the person, at least one of bony geometries, insertion, and origin of soft tissues respectively associated with the person. Furthermore, the at least one computing device accesses at least one musculoskeletal model including at least one of a bone, an implant, and soft tissue, wherein at least an aspect of the model includes a deformable body.

22 Claims, 10 Drawing Sheets

(52) U.S. Cl.
CPC ... *A61B 2034/104* (2016.02); *A61B 2034/105* (2016.02); *A61B 2034/108* (2016.02); *A61F 2002/30948* (2013.01); *A61F 2002/30952* (2013.01); *A61F 2002/30955* (2013.01); *A61F 2002/3895* (2013.01)

(58) Field of Classification Search
CPC ................ A61F 2/3877; A61F 2/30942; A61F 2002/4666; A61F 2002/3895; A61F 2002/4633; A61F 2002/30948; A61F 2002/30952; A61F 2002/30955
USPC .............................................................. 705/2
See application file for complete search history.

(56) References Cited

U.S. PATENT DOCUMENTS

2013/0197887 A1* 8/2013 Raschke ................. G06F 30/00 703/6
2014/0019110 A1 1/2014 Otto et al.
2016/0045317 A1 2/2016 Lang et al.
2018/0360609 A1 12/2018 Steines et al.
2019/0175272 A1 6/2019 Khan et al.
2020/0030034 A1 1/2020 Kontaxis et al.
2020/0275976 A1 9/2020 McKinnon et al.
2020/0357508 A1* 11/2020 Deleu .................... G16H 50/50
2023/0285084 A1 9/2023 McKinnon et al.

OTHER PUBLICATIONS

Shriram Duraisamy et al: ""Biomechanical Evaluation of Isotropic and Shell-Core Composite Meniscal Implants for Total Meniscus Replacement: A Nonlinear Finite Element Study"",IEEE Access, vol. 7 , pp. 140084-140101, XP011749579, DOI: 10.1109/ACCESS. 2019.2943689 [retrieved on Oct. 7, 2019].

Extended European Search Report in EP Application No. 22877284. 4-1122, mailed Jul. 18, 2025 (13 pages).

Shafiq et al., "Marker Detection and Trajectory Generation Algorithms for a MulticameraBased Gait Analysis System", Mechatronics vol. 11, Feb. 28, 2001, Retrieved on Apr. 15, 2016, Retrieved from the internet: URL <https://www.sciencedirect.com/science/article/abs/pii/S09 57 41580000026X?via % 3 Dihub>.

Huang et al., "Exploring the Relationship Between Pain Intensity and Knee moments inParticipants with Medial Knee Osteoarthritis: a Cross-sectional Study", BMC MusculoskeletalDisorders, Aug. 12, 2021, Retrieved on Apr. 15, 2026, Retrieved from the internet: URL<https://link.springer.com/article/ 10.1186/s 12891-021-04587-w>.

Biehl et al., "Towards Planning of Osteotomy Around the Knee with Quantitative Inclusion ofthe Adduction Moment: A Biomechanical Approach", Journal of Experimental Orthopaedics, Jun. 11, 2021, Retrieved on Apr. 15, 2026, Retrieved from the internet: URL <https://link.springer.com/article/ 10.1186/s40634-02 1-00324-3>.

Favre et al. "A Neural Network Model to Predict Knee Adduction Moment DuringWalking Based on Ground Reaction Force and Anthropometric Measurements", Journal ofBiomechanics, Feb. 23, 2012, Retrieved on Apr. 15, 2026, Retrieved from the internet: URL <https:/ /www .sciencedirect.com/science/article/ abs/pii/ S0021929011007603>.

International Search Report and Written Opinion for corresponding PCT Application No. PCT/US2026/014308 dated Apr. 22, 2026 (16 pages).

* cited by examiner

Musculoskeketal model

A
P
M
L
Nodal contact forces

Nodal contact
force (N)
8
7
6
5
4
3
2
1
0
Finite element model

SYSTEM AND METHOD TO ASSESS MECHANICAL OUTCOMES FOLLOWING JOINT ARTHROPLASTY

CROSS-REFERENCE TO RELATED APPLICATIONS

The present application is a U.S. National Stage Application under 35 U.S.C. § 371 of International Patent Application No. PCT/US2022/045117, filed Sep. 28, 2022, which claims priority to U.S. Provisional Patent Application Ser. No. 63/249,327, filed on Sep. 28, 2021, and entitled COMPUTATIONAL WORKFLOW ASSESSING TKA BIOMECHANICS, the entire contents of which are hereby incorporated by reference in their respective entireties.

FIELD

The present disclosure relates, generally, to data management and communications and, more particularly, to a system and method for predicting mechanical outcomes at the joint and fixation (i.e., bone-implant, cement-implant, or cement-bone interface) levels of joint arthroplasty implants.

BACKGROUND

Mechanically related complications, including joint instability or stiffness and aseptic loosening, account for a significant amount of joint arthroplasty failures, in particular for total knee arthroplasty. While instability failures are related to the joint level mechanics after the arthroplasty, like kinematics and kinetics (i.e., loads), aseptic loosening failures are related to the fixation level mechanics, like, the interaction between the implant components and the surrounding bone. Biomechanically, joint level mechanics can be studied, for example, using musculoskeletal multibody dynamics models, where the bones and implants are formulated as rigid (i.e., driven by whole body kinematics captured in a motion analysis laboratory. Such models are useful to evaluate the effect of implant component alignment on joint kinematics and loads, and the interplay between ligament constraints and joint kinematics. Conversely, fixation level mechanics are often studied with finite element models, which formulate the implant and bone as deformable bodies, and are driven by simplified loads or by complex loading conditions, which can be representative of activities of daily living. Finite element models can be used to evaluate the bone-implant interaction, including the risk of cement debonding, the risk of bone failure, the relative micromotion between implant and bone, the motion experienced by the implant, or a combination of these outcome measures for a range of implant designs and component alignments.

FE models have been used to evaluate the risk of bone failure, the micromotion experienced by the implant, or both of these outcome measures for a range of implant designs and component alignments. While such approach has provided detailed information and understanding of the joint level and fixation level mechanics in TKAs, the disconnect between these levels in prior biomechanical analyses hinders understanding of the function of TKA as a whole.

Accordingly, although known approaches provide detailed information regarding joint level and fixation level mechanics in total knee arthroplasty procedures, there remains a disconnect between those levels in biomechanical analyses, which hinders an understanding of total knee arthroplasty functionality as a whole. For example, detailed biomechanical analysis of aspects of total knee arthroplasty biomechanics, such as computational studies, often focus either on the mechanics at the joint level (e.g., joint kinematics and joint loads) or at the fixation level (e.g., bone-implant interaction). This gives rise to the disconnect between joint level mechanics and interface level mechanics, as well as to identifying tradeoffs there-between.

The present system and method address these and other deficiencies in the art, and it is with respect to these and other considerations that the disclosure made herein is presented.

BRIEF SUMMARY

In accordance with one or more implementations of the present disclosure, A computerized system and method to assess joint level biomechanics and fixation level biomechanics of joint arthroplasty devices. At least one computing device, configured by executing instructions stored on non-transitory processor readable media receives preoperative medical information of a person requiring joint arthroplasty. Further, the at least one computing device determines, as a function of at least some of the preoperative medical information of the person, at least one of bony geometries, insertion, and origin of soft tissues respectively associated with the person. Furthermore, the at least one computing device accesses at least one musculoskeletal model including at least one of a bone, an implant, and soft tissue, wherein at least an aspect of the model includes a deformable body. Still further, the at least one computing device accesses information representing at least a functional activity including at least one of kinematics and ground reaction forces, and modifies at least part of the musculoskeletal and finite element models, including by replacing at least one geometry of the musculoskeletal model with at least one geometry associated with the person and by including at least one implant according to a pre-surgical plan. The at least one computing device determines, as a function of at least one simulation of the modified musculoskeletal model, at least one of joint kinematics and at least one of muscle, ligament, and joint contact forces. Moreover, the at least one computing device determines a response of the deformable body using at least one of the determined the joint kinematics and the at least one of muscle, ligament, and joint contact forces. In addition, the at least one computing device assesses the joint level biomechanics and fixation level biomechanics of joint arthroplasty devices as a function of the modified musculoskeletal model and the finite element model, and generates a pre-surgical plan for the person based on the information derived from the interaction between joint level biomechanics and fixation level biomechanics.

In one or more implementations, the musculoskeletal model includes bones and implants represented as rigid bodies, and soft tissues represented as line elements.

In one or more implementations, the implants are intended for, total joint replacement, total knee replacement, or partial joint replacement.

In one or more implementations, the partial joint replacement includes unicompartmental knee replacement or patellofemoral replacement.

In one or more implementations, the soft tissues include muscle, ligament, joint capsule, or other passive structure that does not actively generate force.

In one or more implementations, the at least one computing device optimizes ligament slack lengths of the modified musculoskeletal model to achieve a balanced knee by simulating a clinical intraoperative assessment of joint laxity.

In one or more implementations, the musculoskeletal model includes at least one of a multibody dynamics model and a finite element model.

In one or more implementations, the preoperative medical information includes imaging comprising at least one of a computerized tomography scan, magnetic resonance image, plain radiograph, and biplanar radiograph.

In one or more implementations, the at least one computing device receives demographic data associated with the person including height and weight.

In one or more implementations, at least some of the information representing at least one of kinematics and ground reaction forces is obtained during one or multiple representative activities of daily living.

In one or more implementations, the at least some of the information is obtained by motion analysis techniques, fluoroscopy, wearable sensors, implantable sensors, or sensors embedded in the implant.

In one or more implementations, the ground reaction forces are derived from the kinematics and the characteristics of the subject.

In one or more implementations, the at least some of the information is obtained preoperatively on the person requiring joint arthroplasty.

In one or more implementations, the kinematics and ground reaction forces are determined from a library of kinematics and ground reaction forces on healthy individuals or individuals having received the same joint replacement as the subject by selecting one of the healthy individuals or individuals having received the same joint replacement as the subject having characteristics similar to the person requiring joint arthroplasty.

In one or more implementations, the pre-surgical plan includes a choice of position and rotation of the implant with respect to anatomic landmarks and the design of the implant, including constraint and type of fixation.

In one or more implementations, the at least one computing device determines joint level kinematics from whole body kinematics using inverse kinematic optimization.

In one or more implementations, the at least one computing device determines joint level kinematics and joint, ligament, and muscle forces using a forward dynamic simulation.

In one or more implementations, the at least one computing device scales and aligns segments of the musculoskeletal model.

In one or more implementations, the at least one computing device identifies, as a function of assessing the joint level biomechanics, a tradeoff between the person's knee kinematics and/or ligament mechanics and/or knee forces at the articular surfaces, and micromotion and/or risk of bone failure and/or risk of cement debonding of at least one of the implants interface.

In one or more implementations, the at least one computing device improves, as a function of information using the joint level mechanics and the interface level mechanics, the choice of implant design and position to maximize at least one of implant longevity and function.

Additional features, advantages, and embodiments of the disclosure may be set forth or apparent from consideration of the detailed description and drawings. It is to be understood that the foregoing summary of the disclosure and the following detailed description and drawings provide non-limiting examples that are intended to provide further explanation without limiting the scope of the disclosure as claimed.

BRIEF DESCRIPTION OF THE DRAWINGS

Aspects of the present disclosure will be more readily appreciated upon review of the detailed description of its various embodiments, described below, when taken in conjunction with the accompanying drawings, of which.

DETAILED DESCRIPTION OF CERTAIN IMPLEMENTATIONS

Figure 1:
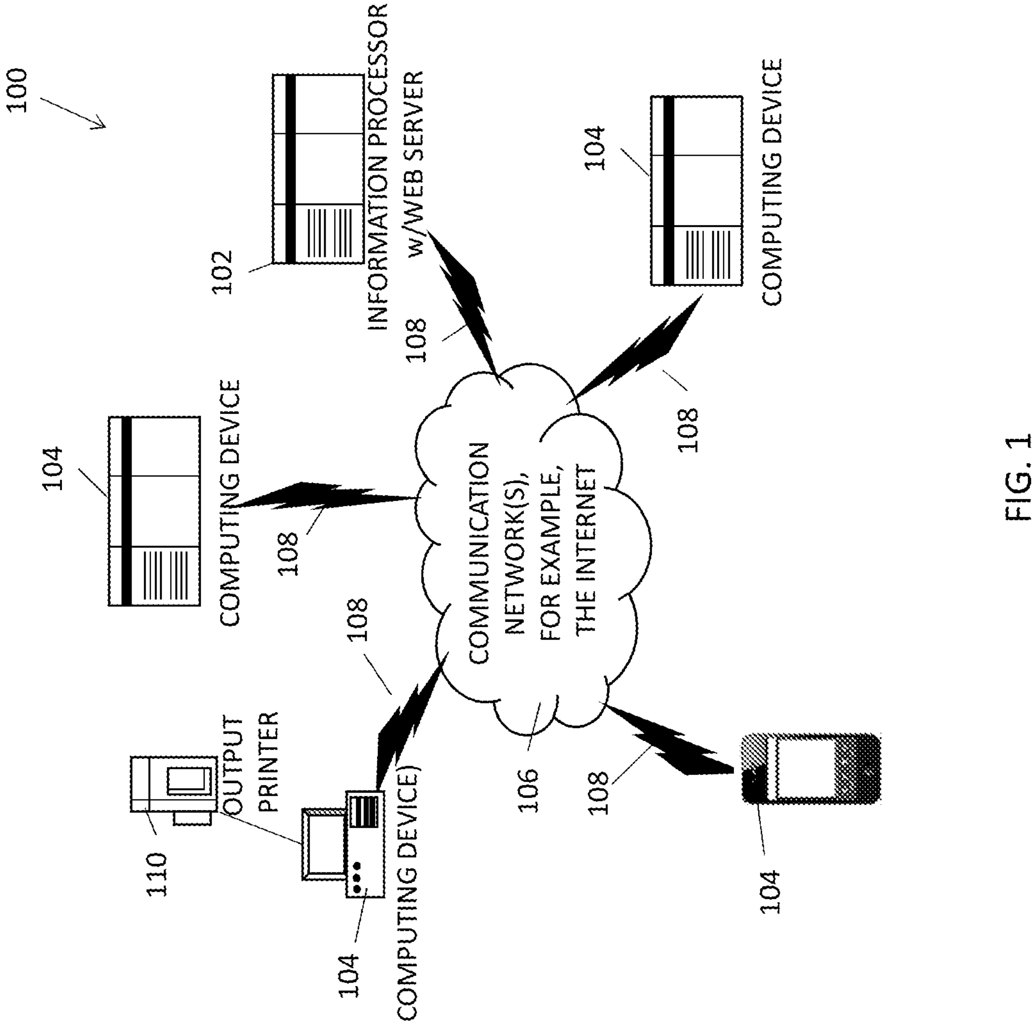
FIG. 1 is a block diagram illustrating an example implementation of the present disclosure and that represents a plurality of devices and the flow of information associated with the devices.

By way of introduction and overview, the present disclosure addresses a dichotomy between joint level mechanics and fixation level mechanics, and is usable to improve the biomechanical understanding, including of joint function and fixation after arthroplasty. Joint biomechanics can be assessed simultaneously at the joint and fixation levels via a computerized simulation environment, for example, that integrates the outputs from musculoskeletal models and coupled with finite element models. The combination can be used to determine the choice of the implant, for example, its position, orientation, constraint, and/or design for optimal joint and fixation mechanics. Information can be generated and used for a patient-specific surgical plan, including for the component design, position, and soft tissue balance to improve the longevity and function of an implant. As such, the present workflow can be included in optimization routines to select the optimal design and position of an implant, based on the joint level and fixation level mechanics.

As an example, this approach can investigate the effect if tradeoffs in implant design and position on the joint mechanics (e.g., anterior-posterior translation of the knee) at the articular surfaces (on one hand), and the fixation mechanics (e.g., motion of the implant and risk of failure at the cement-implant interface) (on the other).

Accordingly, the combined joint level and fixation level mechanics in the integrated workflow of the present disclosure can be used to evaluate knee biomechanics, including to demonstrate the influence of joint kinematics on the bone-implant interaction. Identifying the tradeoffs described herein can improve implant longevity including by generating a patient-specific surgical plan in terms of component position, design, and/or constraint based on the information derived from the interaction between joint level mechanics and fixation level mechanics.

In operation, musculoskeletal simulations of respective activities can be performed, for example, using a model having a 12 degree-of-freedom knee joint, to determine the joint kinematics, joint loads, and ligaments and muscle loads. Information regarding the joint kinematics and loads and ligaments and muscle loads can be used as inputs to a finite element model virtually implanted with an insert having the same articular geometry as used in the musculoskeletal model to simulate the fixation mechanics.

Thus, the present disclosure includes technology to provide information regarding implant design, surgical technique, and patient factors that can impact the tradeoffs between joint level and fixation level mechanics. By relating the joint level to the fixation level mechanics, implant migration can be identified, which can occur when the loads transferred during activities of daily living exceed the strength of the bone, leading to eventual collapse. This information can be utilized to generate a patient-specific surgical plan to decide on the component design, position, and soft tissue balance to improve the longevity and function of the implant. As such, the present workflow can be included in optimization routines to select the optimal design and position of the implant, based on the joint level and fixation level mechanics.

A workflow is provided to assess holistically joint biomechanics after joint arthroplasty to provide information usable to identify the tradeoffs between joint level mechanics (e.g., joint kinematics and joint loads) and fixation level mechanics. More particularly, a musculoskeletal model is usable to determine the joint kinematics and loads, which is combined with a finite element model that, using joint loads as input, can be used to determine bone-implant micromotion and bone strains.

In one or more implementations, patient-specific musculoskeletal modeling of a lower limb is used. In one or more non-limiting examples, generic software, like OPENSIM can be used for the generic musculoskeletal modeling. The joint under study can be modeled, for example, using generic available plugins that allow multiaxial motions, like the JOINT AND ARTICULAR MECHANICS ("JAM") toolbox The model can comprise three-dimensional (3D) rigid body segments of the pelvis, thighs, shanks, feet, torso, and head, as well as 44 Hill-type muscle-tendon units. Thereafter, the formulation of the joint or joints under study can incorporate the soft tissue envelope of the said joint. For example, in one or more formulations, the soft tissue envelope of a knee joint can be modeled as comprising 12 non-linear, tension only, springs to represent the patellar tendon, medial collateral ligament (superficial and deep), lateral collateral ligament, posterior cruciate ligament (anterolateral and posteromedial), popliteofibular ligament, posteromedial capsule, posterior capsule, iliotibial band, and medial and lateral patellofemoral ligaments. The virtual representation of the knee can include any contact algorithm that allows relative translation of the articulating surfaces and can compute the contact forces between two surfaces, like but not limited to, an elastic foundation contact model.

The geometries of the bones and the insertions of soft tissues, like the muscle-tendon units or the ligaments can, thereafter, be adapted to any subject by incorporating patient-specific geometries and properties derived from any type of imaging, like, but not limited to, CT-scans or MRI. The force generating properties of each muscle, like the maximum isometric properties, fiber length, and tendon slack length can be obtained, for example as known to one of ordinary skill in the art. Moreover, information representing stiffness, reference strains at full extension of the ligaments of the joint under study can be obtained, for example as known to one of ordinary skill in the art. In one or more implementations, both models can share the same mesh (i.e., discretization) of the articular surfaces.

It is recognized herein that some uncertainty may exist, such as due to a lack of appropriate data for the subject of study, that may prevent subject-specific modeling. In one or more implementations, the bones and soft tissue properties (e.g., insertion points, slack length, and/or optimal fiber length of muscle-tendon units and/or insertion points and reference stiffness and strains ligaments) can be adapted from a generic musculoskeletal model by scaling can be derived, such as from anatomical literature. The workflow of the present disclosure can quantify the influence of uncertainties in anatomical properties on joint and fixation mechanics, such as by using Monte Carlo analyses or a design of experiments approach.

In one or more implementations, simulations of activities with the musculoskeletal model are performed involving a three-step process. In a non-limiting example, algorithms provided via the JAM toolbox can be applied. At the outset, the equilibrium position of the knee joint and the ligament slack lengths are determined with iterative passive forward dynamic simulations of the knee in full extension using motion capture data. The ligament slack lengths can be optimized to achieve the surgical goal of a "well-balanced" knee, by ensuring equal forces in the medial and lateral compartments of the knee or by ensuring equal medial-gaps when reproducing a standard intraoperative exam, like varus-valgus stress test throughout flexion or at specific flexion angles. The joint kinematics during the said activity can be obtained by multiple methods, including but not limited to from motion capture data using, for example, inverse kinematic optimization, from wearable sensors, from single plane or biplanar fluoroscopy, or any other method that allows deriving the motions of the joint under study throughout activities. In one non-limiting example, if inverse kinematic optimization is used, the knee can be considered a 1 degree-of-freedom joint, for which the implanted total knee arthroplasty-specific secondary kinematics can be previously determined through a passive forward dynamic simulation of knee flexion from 0° to 70°. Thereafter, an algorithm to determine joint mechanics, such as, but not limited to, the concurrent optimization of muscle activation and kinematics (COMAK) algorithm, can be used to determine the joint mechanics and the muscle, ligament, and joint contact forces during the activity. During this step, all degree-of-freedom of the joints can be active. More particularly, the objective function used for the algorithm, for example COMAK algorithm, can comprise a combination of the muscle and joint forces, such as the sum of squared muscle activity weighted by muscle volume, with the net knee joint contact energy weighted by a constant regularization term.

In another configuration, the model can be driven with a forward dynamic predictive model using data such as, but not limited to, electromyographic signals, muscle forces, and joint kinematics and kinetics under a given activity, in case information representing the kinematics of the patient or the ground reaction forces is unavailable.

In an implementation of the present disclosure, a functional activity can be simulated in accordance with the teachings herein. The magnitude of the forces in one or more compartments of the joint under study can be evaluated for the activity. In addition, the contact positions between any two components of the implant in any direction can be quantified in one or more compartments as the location of the center of pressure with respect to, for example, the geometric center of the component. Still further, the maximum translation in any direction can be computed for one or more compartments of the joint under study as the difference between the extremes of the positions of the contact points in any compartment during the activity.

In addition to musculoskeletal modeling, one or more finite element models can be developed, for example, from the preoperative CT-scans of the subject, with the implants placed according to surgeon preference or to an optimized position to maximize longevity and function of the total knee arthroplasty. The relative position between the implants and bones in said finite element models match that of the musculoskeletal model.

The bones and implants in the finite element models implanted knees can be meshed (i.e., discretized), for example, with, but not limited to, linear tetrahedral elements. In a non-limiting example, ABAQUS by DASSAULT SYSTÈMES can be used. As an example, the edge length of the elements can transition from 1 mm at the bone-implant interface to 3.5 mm at the end of the bone. For the implant components, the edge length of the elements can be, for example 1 mm. The components in the finite element model are meshed such that the mesh at the articular surface matches that in the musculoskeletal model. In other words, the number of nodes and elements and their locations match in the musculoskeletal and finite element models.

Continuing with the present example, the implant components can be modeled as, for example, linear, isotropic, and homogenous materials. Some areas can be modeled, for example, as TRABECULAR TITANIUM 3D-printed porous material (e.g., from LIMACORPORATE) and assigned properties based on manufacturer's specifications: E=1.1 GPa and v=0.3. Other parts, can be modeled, for example, as solid Ti6Al4V titanium alloy (E=114.3 GPa, v=0.33). Furthermore, and as noted above with regard to the musculoskeletal model, the tibial insert can be modeled as UHMWPE (E-463 MPa, v=0.46). In such case, the bone can be assumed to be, for example, a linear, isotropic, and non-homogenous material, although alternatives are envisioned herein, such as bone being modeled as non-isotropic material or with other suitable models, such as a crushable foam model. The elastic modulus can be dependent on the apparent density of the bone and the Poisson's ratio of 0.3. The apparent bone density can be calculated by linearly interpolating the Hounsfield Units (HU) of the CT scan data from each bone into the finite element mesh. In one or more implementations, reference phantoms can be used to determine the relationship between HU and bone mineral density.

In another implementation, reference phantoms are not used during the acquisition of the CT data and, instead, a relationship between HU and bone mineral density can be determined by a phantomless method, like but not limited to considering that the average minimum and maximum HU values of the bone have bone densities of 0 g/cc and 1.8 g/cc, respectively. Still further, the elastic modulus of the bone can be determined by combining a series of empirical equations that describe the density-modulus relationship of the tibia.

For the interaction between the implant and the bone, the initial post-operative period during which bone ingrowth has not yet occurred can be considered. To this end, the bone-implant interfaces can be modeled with frictional, line-to-line contact (i.e., with no interference fit) to consider a worse-case scenario for the interaction between the implant and the bone. The bone-implant interfaces can also include modeling of press-fit to consider a realistic scenario. In one or more implementations, the coefficient of friction between the bone and the 3D-printed TRABECULAR TITANIUM can be set to 1.1 or other suitable value, for example, according to specifications provided by the manufacturer. The coefficient of friction between the bone and solid titanium alloy can be set to 0.6 or other suitable value. Moreover, each bone can be fully constrained at the end furthest from the implant, and the different components of the implant to be rigidly bonded together, for example, by bonding the UHMWPE insert to the implant's baseplate.

Continuing with the present example, the musculoskeletal and finite element models can be, thereafter, integrated, including to apply the loads calculated with the musculoskeletal model to the finite element models, accounting for the tibiofemoral kinematics. At the outset, the nodes of the insert's articular surface that experience load at some point during the stance phase of gait can be identified in the musculoskeletal model. Thereafter, the location and the profile of the force components of each of these nodes can be extracted. For each node in the musculoskeletal model experiencing load, the matching node or closest node can be determined on the insert's articular surface of the finite element model, and the corresponding 3D force profiles extracted from the musculoskeletal model applied.

Although many of the examples and references herein regard use of musculoskeletal and finite element models, the present disclosure is not so limited. It is envisioned herein that alternative implementations can utilize a single model, including for bones, implants, muscles, and ligaments. In such case(s), at least the implants and surrounding bone can be modeled as deformable parts, while other regions of the body can be modeled as rigid or deformable elements.

Continuing with reference to integrating the musculoskeletal and finite element models, the bone-implant micromotion can be computed at each point for the activity as the difference in displacement between each pair of closest bone-implant interfacial nodes. The micromotion can be compared against the experimentally determined thresholds for bone ingrowth, which can range, for example, from 20 μm to 50 μm, or against thresholds for fibrous tissue formation, which can be, for example, 150 μm. Moreover, the bone at risk of failure can be quantified by comparing the compressive and tensile principal bone strains against the yield strain of the bone which can be, for example, for the tibial cancellous bone: −7300 με in compression and 6500 με in tension. The bone at risk of failure can also be quantified through iterative simulations to capture the progressive collapse of the bone, when using an appropriate material model, like a crushable foam model. The relative bone volume at risk of failure can be computed at each point during the respective stance phase, for example, by dividing the volume of bone at risk of failure (i.e., with strains greater than yield) by the total volume of, for example, interfacial bone. Moreover, the composite micromotion can be quantified as the largest value of micromotion at each implant interfacial node across the activity. Similarly, the composite risk of bone failure can be quantified as the largest value of the risk of bone failure at each bone element at across the activity. Thereafter, the composite bone volume at risk of failure can be calculated, as specified above. Other variables important for the fixation mechanics, such as stress shielding, cement mantle failure, cement-bone debonding, or implant-cement debonding may be also considered in one or more implementations.

Referring now to FIG. 1, a block diagram is shown illustrating an example implementation of the present disclosure and that represents an association of a plurality of devices and the flow 108 of information associated with the devices. In the example shown in FIG. 1, various computing devices 102 and 104 are shown, each capable of executing desktop and/or mobile computing device web browser application(s) including MICROSOFT EDGE, INTERNET EXPLORER, CHROME, FIREFOX, and other (e.g., SAFARI, OPERA). In addition to standard web browser application functionality, user information can be gathered via Push Notifications, and information can be retrieved from a computing device using a "REST" interface. Various mobile devices running different operating systems are shown, including IOS, ANDROID and other (e.g., PALM, WINDOWS or other mobile device) operating system.

In the example shown in FIG. 1, one or more data processing apparatuses 102 is operatively coupled to one or more user computing device(s) 104. Devices 102/104 can be respectively operated by one or more users skilled in the use of the proposed workflow, included, but not limited to, healthcare providers and associated staff, medical specialists, and/or biomechanical specialists. Healthcare providers can include, for example, physicians, physician assistants, nurses, therapists and/or other providers of healthcare services. Biomechanical specialist can include, for example, engineers specialized in biomechanics. Data processing apparatus 102 and/or user computing device 104 can be operable to access and/or store various information on database(s) 103-including, for example, historic medical and procedure information patients, physicians, devices, or the like.

Also illustrated in FIG. 1 is a network 106, which can be configured as a local area network (LAN), wide area network (WAN), Peer-to-Peer network ("P2P"), Multi-Peer network, the Internet, one or more telephony networks or a combination thereof, that is operable to connect data processing apparatus 102 and/or devices. Though many of the examples and implementations shown and described herein relate to product and/or service recommendations, many other forms of content can be provided and/or delivered by system 100.

Figure 2:
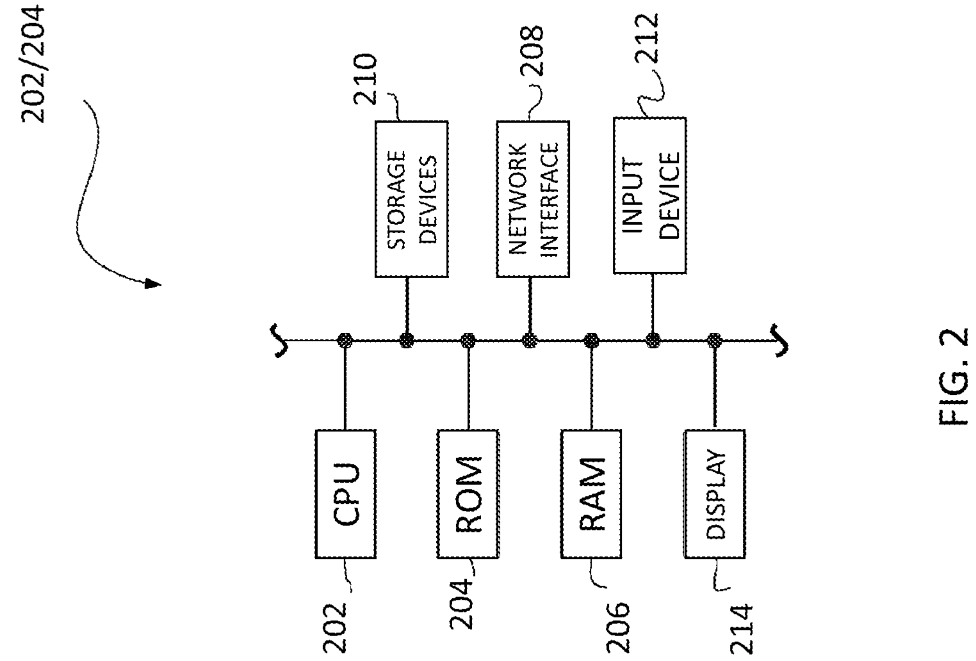
FIG. 2 is a block diagram that illustrates functional elements of one or more of a data processing apparatus or computing device.

FIG. 2 is a block diagram that illustrates functional elements of one or more of data processing apparatus 102 or computing device 104 and preferably include one or more central processing units (CPU) 202 used to execute software code in order to control operations, including of data processing apparatus 102, read only memory (ROM) 204, random access memory (RAM) 206, one or more network interfaces 208 to transmit and receive data to and from other computing devices across a communication network, storage devices 210 such as a hard disk drive, solid state drive, floppy disk drive, tape drive, CD-ROM or DVD drive for storing program code, databases and application code, one or more input devices 212 such as a keyboard, mouse, track ball and the like, and a display 214.

The various components of devices 102 and/or 104 need not be physically contained within the same chassis or even located in a single location. For example, storage device 210 can be located at a site which is remote from the remaining elements of computing devices 102 and/or 104 and can even be connected to CPU 202 across communication network 106 via network interface 208.

The functional elements shown in FIG. 2 (designated by reference numbers 202-214) are preferably of the same categories of functional elements preferably present in computing device 102 and/or 104. However, not all elements need be present, for example, storage devices in the case of mobile computing devices (e.g., smartphones), and the capacities of the various elements are arranged to accommodate expected user demand. For example, CPU 202 in computing device 104 can be of a smaller capacity than CPU 202 as present in data processing apparatus 102. Similarly, it is likely that data processing apparatus 102 will include storage devices 210 of a much higher capacity than storage devices 210 present in computing device 104. Of course, one of ordinary skill in the art will understand that the capacities of the functional elements can be adjusted as needed. For example, one or more graphics processing units (GPU) can be utilized for processing and providing functionality shown and described herein. In addition, or in the alternative, a cluster of computing devices can work to provide functionality shown and described herein.

The nature of the present disclosure is such that one skilled in the art of writing computer executed code (software) can implement the described functions using one or more or a combination of a popular computer programming language including but not limited to C++, JAVA, ACTIVEX, HTML, XML, ASP, SOAP, IOS, OBJECTIVE C, ANDROID, TORR, PYTHON, MATLAB, and various web application development environments.

As used herein, references to displaying data on computing device 104 refer to the process of communicating data to the computing device 104 across communication network 106 and processing the data such that the data can be viewed on the user computing device 104 display 214 using a web browser, custom application or the like. The display screens on computing devices 102/104 present areas within system 100 such that a user can proceed from area to area within the system 100 by selecting a desired link. Therefore, each user's experience with system 100 will be based on the order with which(s) he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of system 100.

Figure 3:
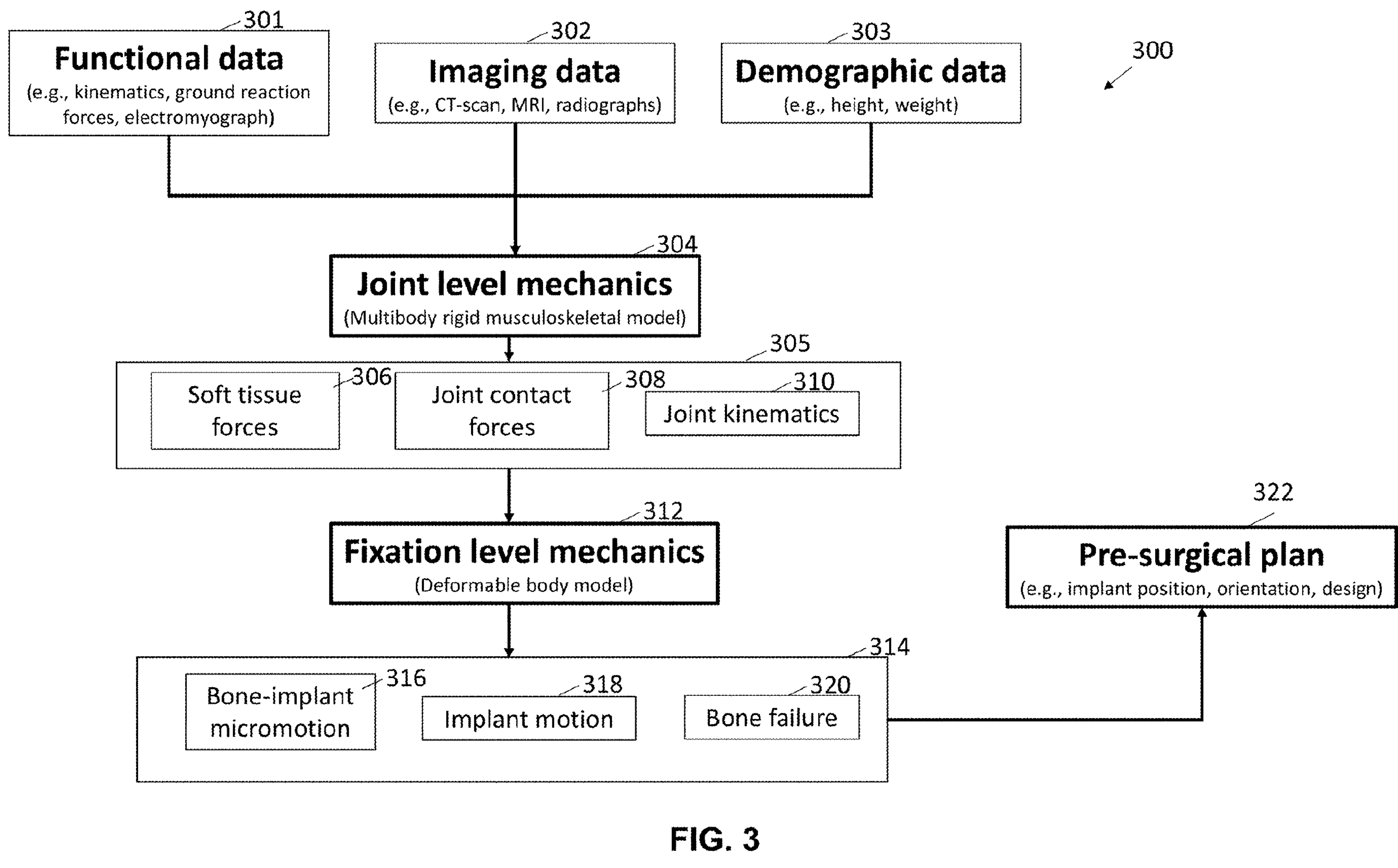
FIG. 3 illustrates a computational workflow, in accordance with an example implementation of the present disclosure.

FIG. 3 illustrates a computational workflow 300, in accordance with an example implementation of the present disclosure. Workflow 300 integrates a multibody rigid musculoskeletal model to determine the joint level mechanics 304, with a deformable body model 312 to evaluate the fixation level mechanics. The outcomes 305 of the joint level mechanics can include The deformable body model 312 could be a finite element model. Both models include subject-specific bony geometry, derived from imaging data 302. As illustrated in FIG. 3, functional data 301 can include kinematics, ground reaction forces and electromyography measurements. Imaging data 302 can include computerized tomography scans, magnetic resonance imaging, and radiographs. Demographic data 303 can include height and weight. These aspects 301, 302, and 303 can be used in joint level mechanics 304, including as a function of musculoskeletal modeling. The outputs of the joint level mechanics model 305 can include soft tissue forces 306, joint contact forces 308, and joint kinematics 310.

Continuing with reference to the workflow shown in FIG. 3, output 305 from the musculoskeletal modeling 304 can be provided to a deformable body model 312 to determine the fixation level mechanics. The deformable body model 312 can be a finite element model. Outputs 314 from the fixation level mechanics 312 can include bone-implant micromotion 316, implant motion 318, and risk of bone failure 320. Outputs related to joint mechanics 305 and fixation mechanics 314, obtained through integration of the joint level mechanics multibody musculoskeletal model 304 and the deformable body model 312 are used to define a pre-surgical plan 322 in terms of the position, orientation, and design of the implant.

Figures 4A, 4B, 4C:
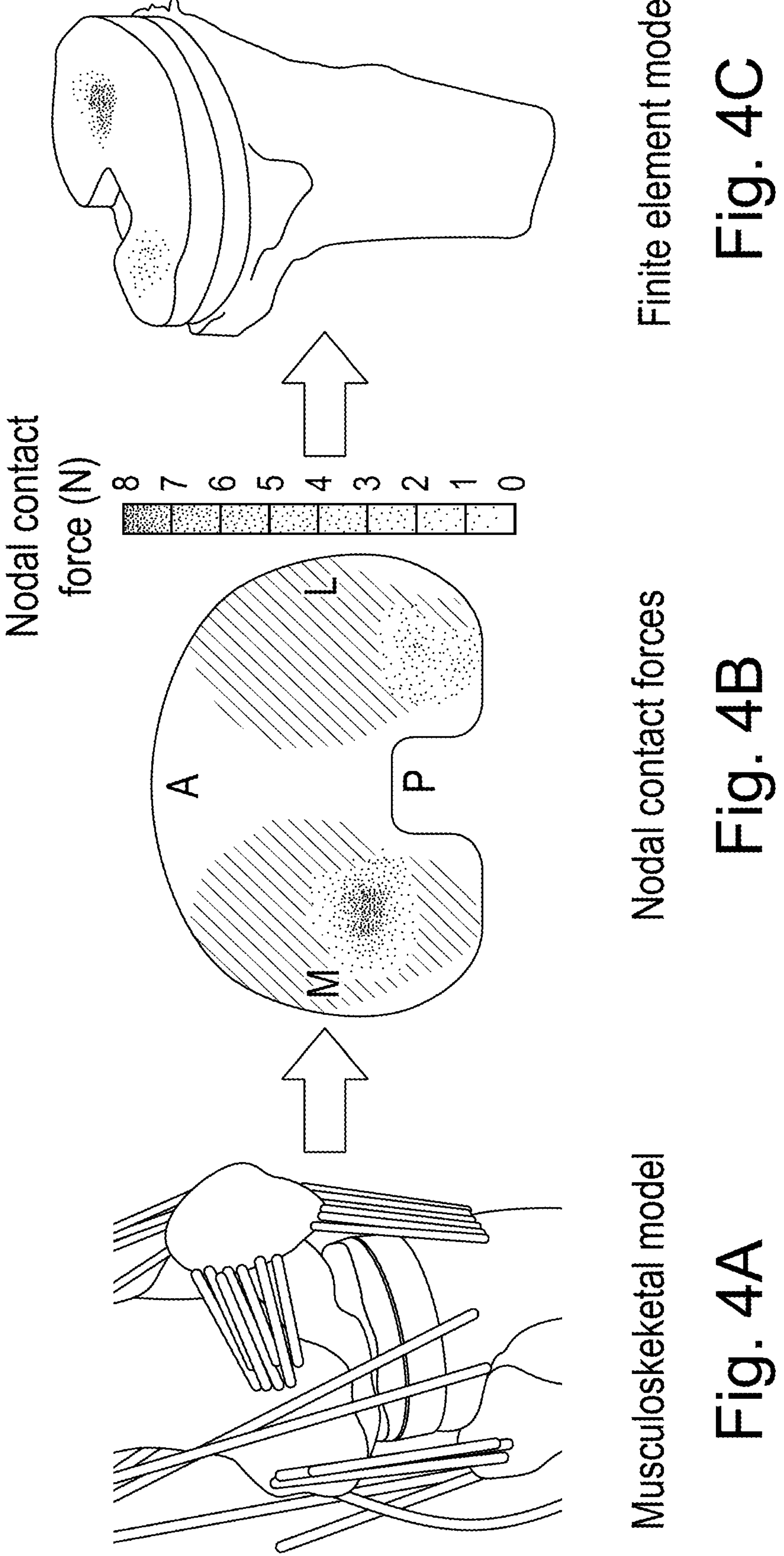
FIG. 4 illustrates an overview of an approach used to connect musculoskeletal and finite element models, in accordance with an example implementation of the present disclosure.

FIG. 4 illustrates an overview 400 of an approach used to connect the musculoskeletal and finite element models, in accordance with an example implementation of the present disclosure. The musculoskeletal and finite element models have matching meshes at the articular surfaces. In other words, the number and location of the nodes in the articular surface of the musculoskeletal model matches exactly the number and location of the nodes of the surface in the finite element model. The musculoskeletal model 402 is used to predict the tibiofemoral joint contact forces during the stance phase of gait 404 at each node of the articular surface. Thanks to the matching nodes between musculoskeletal and finite element surface nodes, these nodal contact forces are then assigned to corresponding nodes on the surface of the insert geometry in the finite element models 406 and used as the loading conditions that drive the finite element simulations.

Figures 5A, 5B:
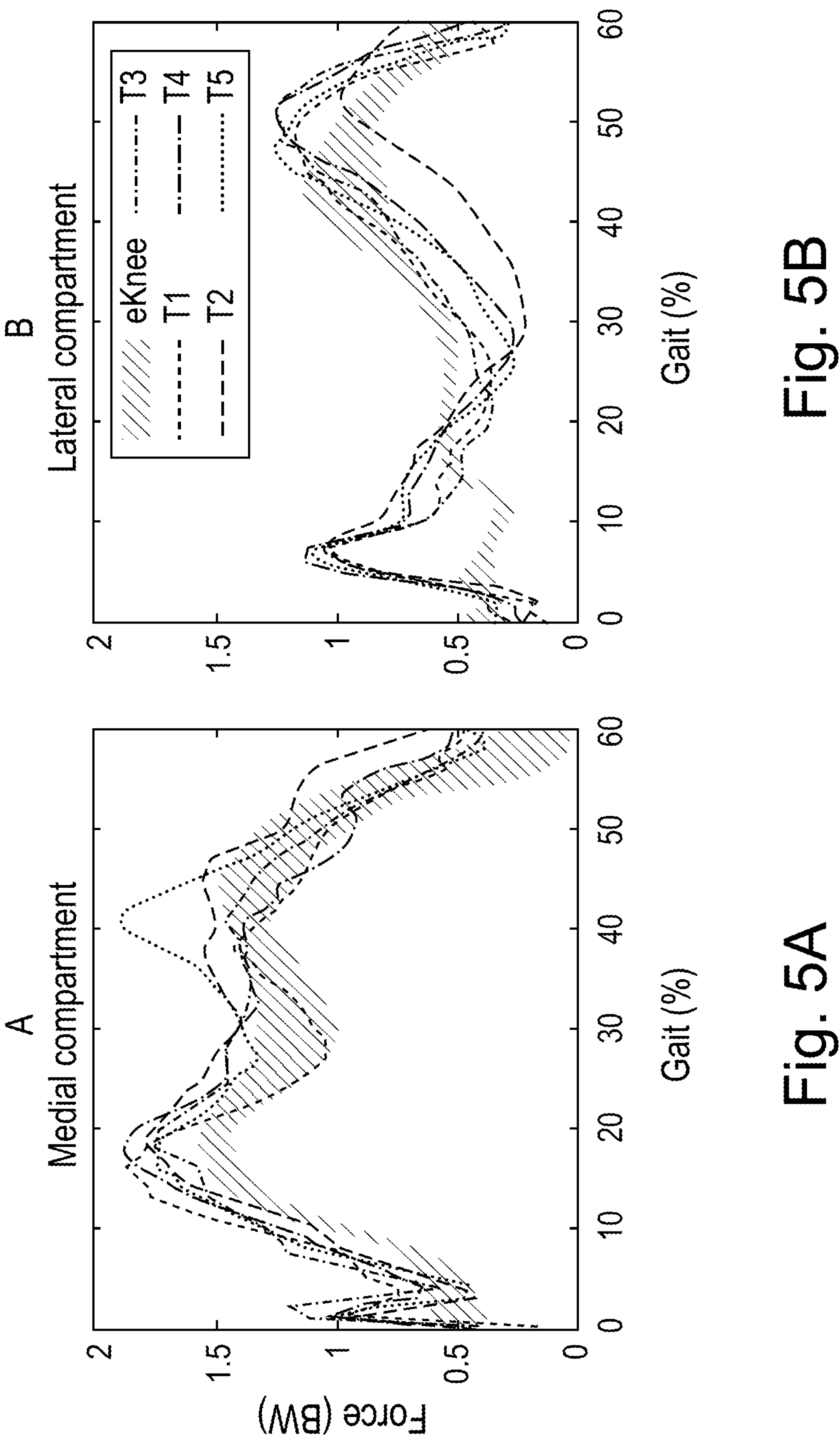
FIGS. 5A and 5B are graphs illustrating tibiofemoral contact forces in bodyweight for the medial compartment and the lateral compartment of the knee joint, in accordance with an example implementation of the present disclosure.

FIGS. 5A and 5B are graphs illustrating tibiofemoral contact forces in bodyweight (BW) for the medial compartment (FIG. 5A) and the lateral compartment (FIG. 5B) of the knee joint, in accordance with an example implementation of the present disclosure. The tibiofemoral contact forces shown in FIGS. 5A and 5B are during the respective stance phase of gait, from heel strike (0% of gait) to toe-off (60% of gait). Each line represents a respective force predicted by the musculoskeletal simulations for a trial (total of five trials, T1-T5), in accordance with the teachings herein. The grey region represents the average +1 standard deviation of the in vivo measurements of the joint contact force with an instrumented implant during the respective five trials.

Figures 6A, 6B:
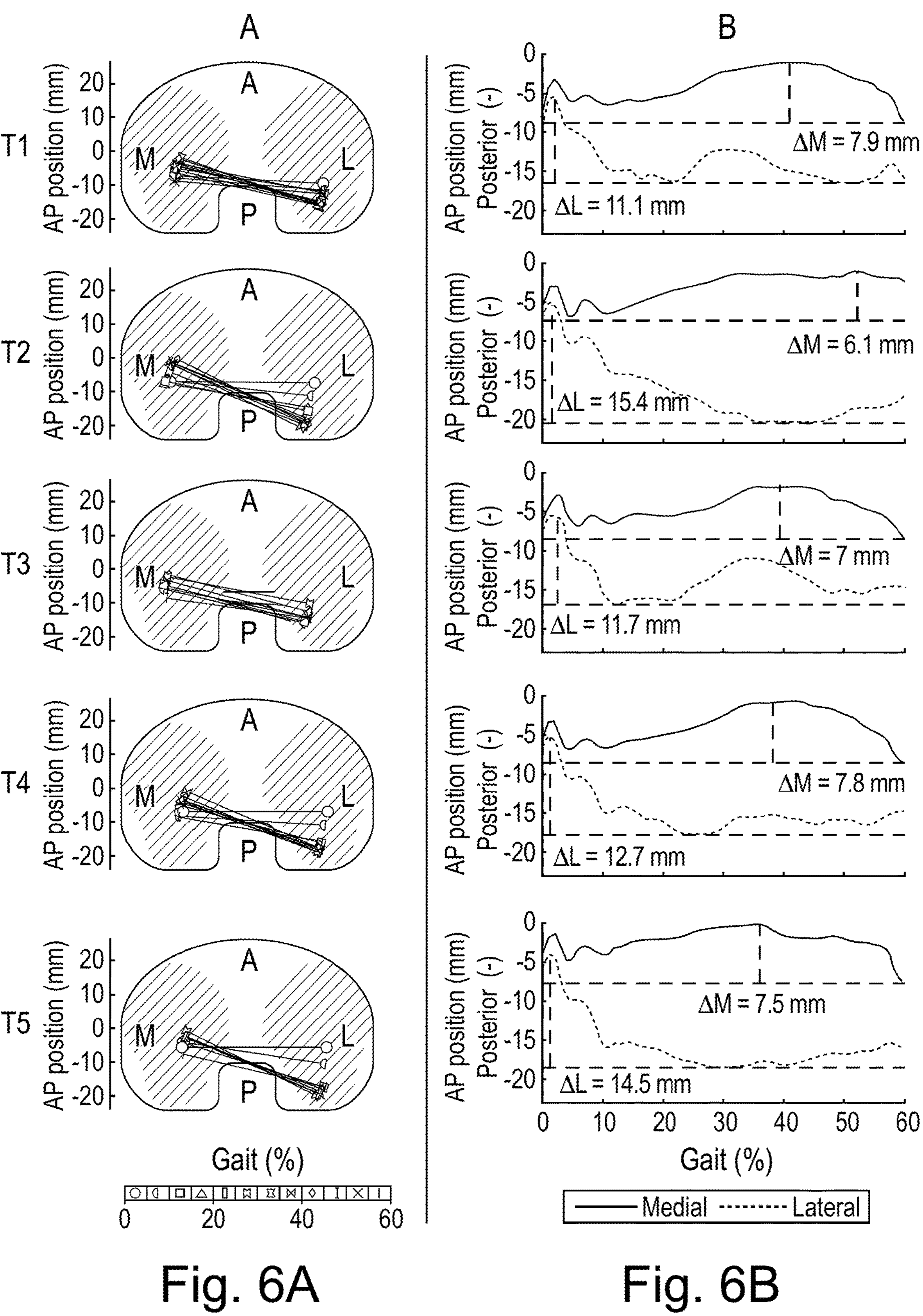
FIGS. 6A and 6B illustrate example respective contacts center of pressure and AP translation during stance phase, in accordance with an example implementation of the present invention.

FIGS. 6A and 6B illustrate example respective contacts center of pressure and AP translation during stance phase, in accordance with an example implementation of the present invention. FIG. 6A illustrates the respective location of the medial and lateral tibiofemoral contact center of pressure during stance of gait, from heel strike (0% of gait) to toe-off (60% of gait), for five trials, T1-T5. FIG. 6B illustrates corresponding anterior-posterior (AP) position of the medial and lateral compartments, showing the total AP translation during stance phase, calculated as the difference between the most anterior and most posterior position of the center of pressure.

Figures 7A, 7B:
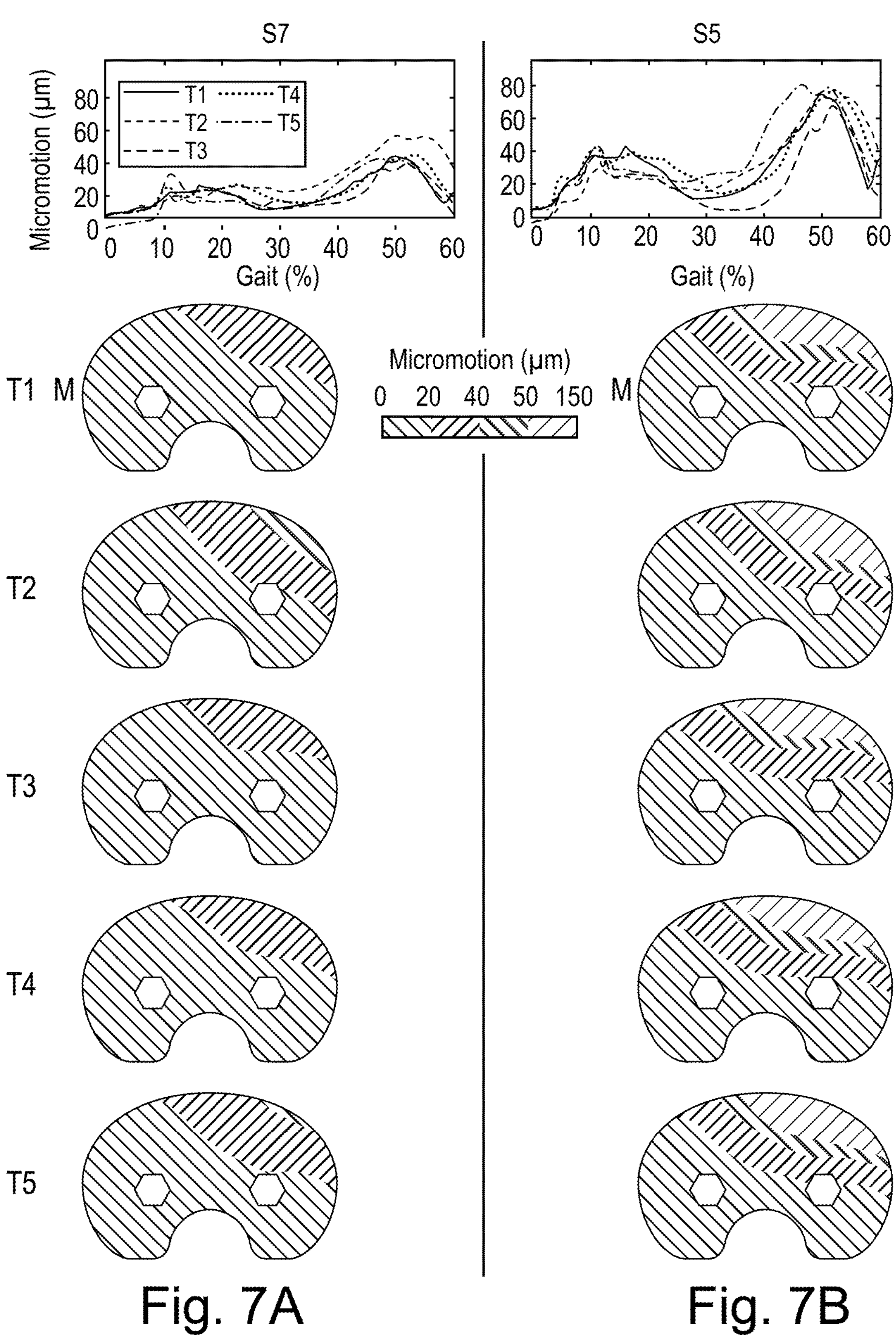
FIGS. 7A and 7B illustrate the evaluation of the bone implant micromotion, in accordance with an example implementation of the present disclosure.

FIGS. 7A and 7B illustrate the evolution of the bone implant micromotion, in accordance with an example implementation of the present disclosure. FIG. 7A illustrates the largest evolution of bone implant micromotion during the respective stance phase of gait, from heel strike (0% of gait) to toe-off (60% of gait), and includes contour plots of the composite bone-implant micromotion for the five gait trials for the subject with the smallest micromotion, S7. FIG. 7B illustrates the largest evolution of bone implant micromotion during the respective stance phase of gait, from heel strike (0% of gait) to toe-off (60% of gait), and includes contour plots of the composite bone-implant micromotion for the five gait trials for the subject with the largest peak micromotion, S5. For the contour plots, the area of the implant above the bone ingrowth threshold of 50 μm is also shown.

Figures 8A, 8B:
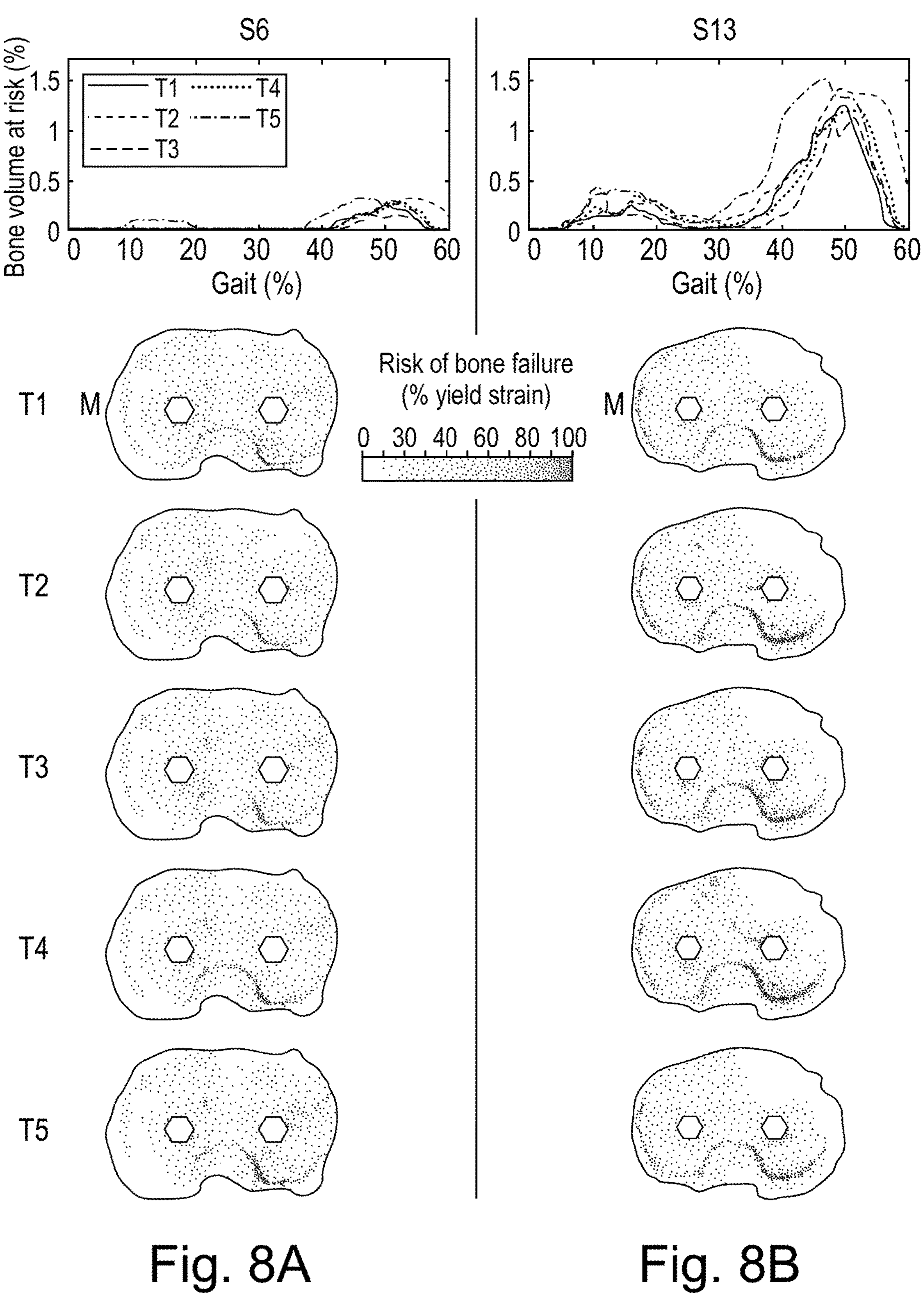
FIGS. 8A and 8B illustrate the evaluation of the bone volume at risk of failure, in accordance with an example implementation of the present disclosure.

FIGS. 8A and 8B illustrate the evolution of the bone volume at risk of failure, in accordance with an example implementation of the present disclosure. FIG. 8A illustrates risk of failure during the stance phase of gait, from heel strike (0% of gait) to toe-off (60% of gait), and contour plots of the composite bone at risk of failure for the five gait trials for the subject with the smallest amount of bone at risk of failure, S6. FIG. 8B illustrates risk of failure during the stance phase of gait for the subject with the largest amount of bone at risk of failure, S13. For the contour plots, the bone at risk of failure is also shown.

Figures 9A, 9B:
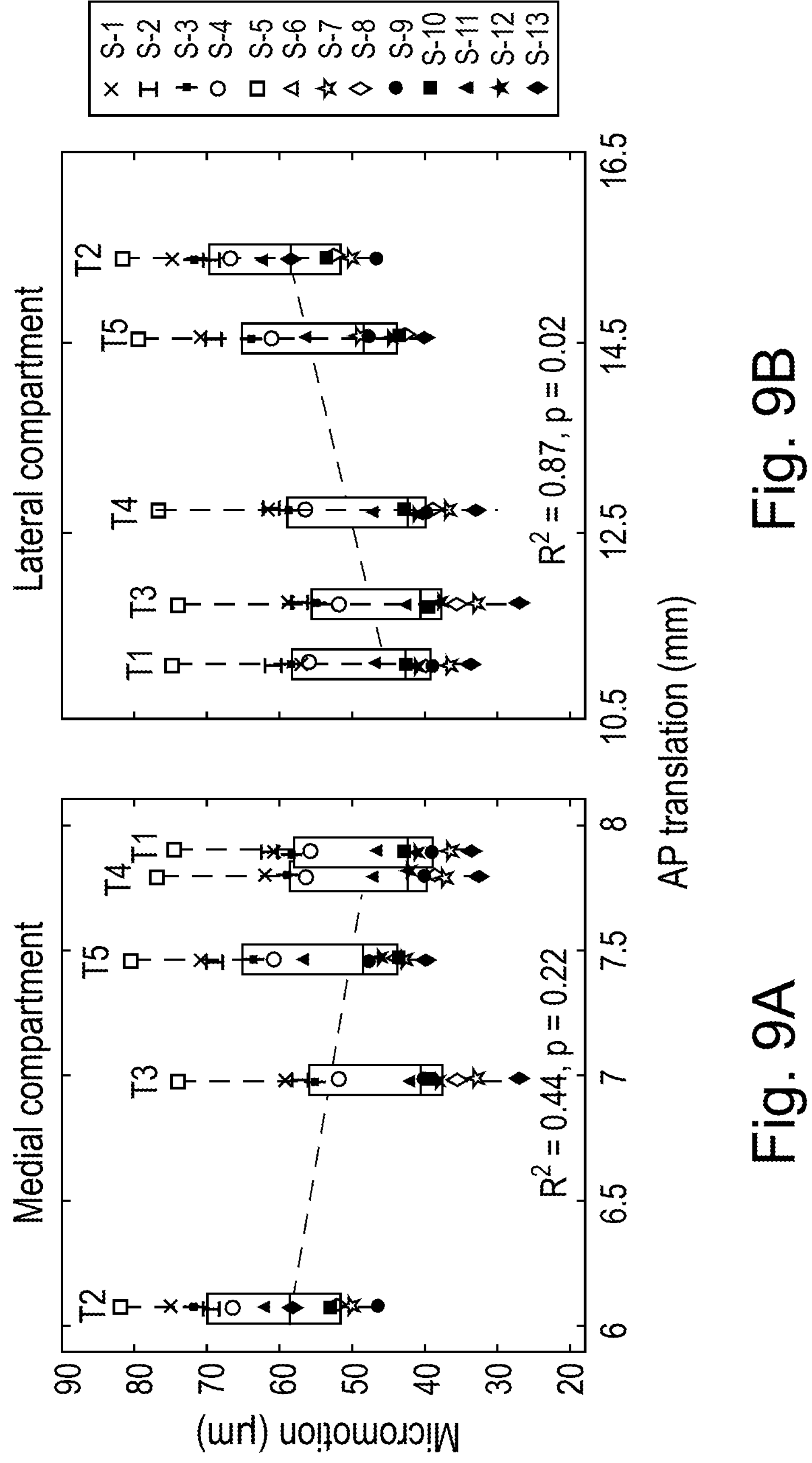
FIGS. 9A and 9B illustrate an example correlation between the maximum anterior-posterior translation for the medial compartment and lateral compartment and peak bone-implant micromotion during the stance phase of gait, respectively.

FIGS. 9A and 9B illustrate an example correlation between the maximum anterior-posterior (AP) translation for the medial compartment and lateral compartments and the peak bone-implant micromotion during the stance phase of gait, respectively. The example correlation shown in FIGS. 9A and 9B is from heel strike to toe-off, for five gait trials. Each point corresponds to a given subject and gait trial. The dashed black lines represent the linear regression relationship between maximum AP translation and the bone-implant micromotion.

Figures 10A, 10B:
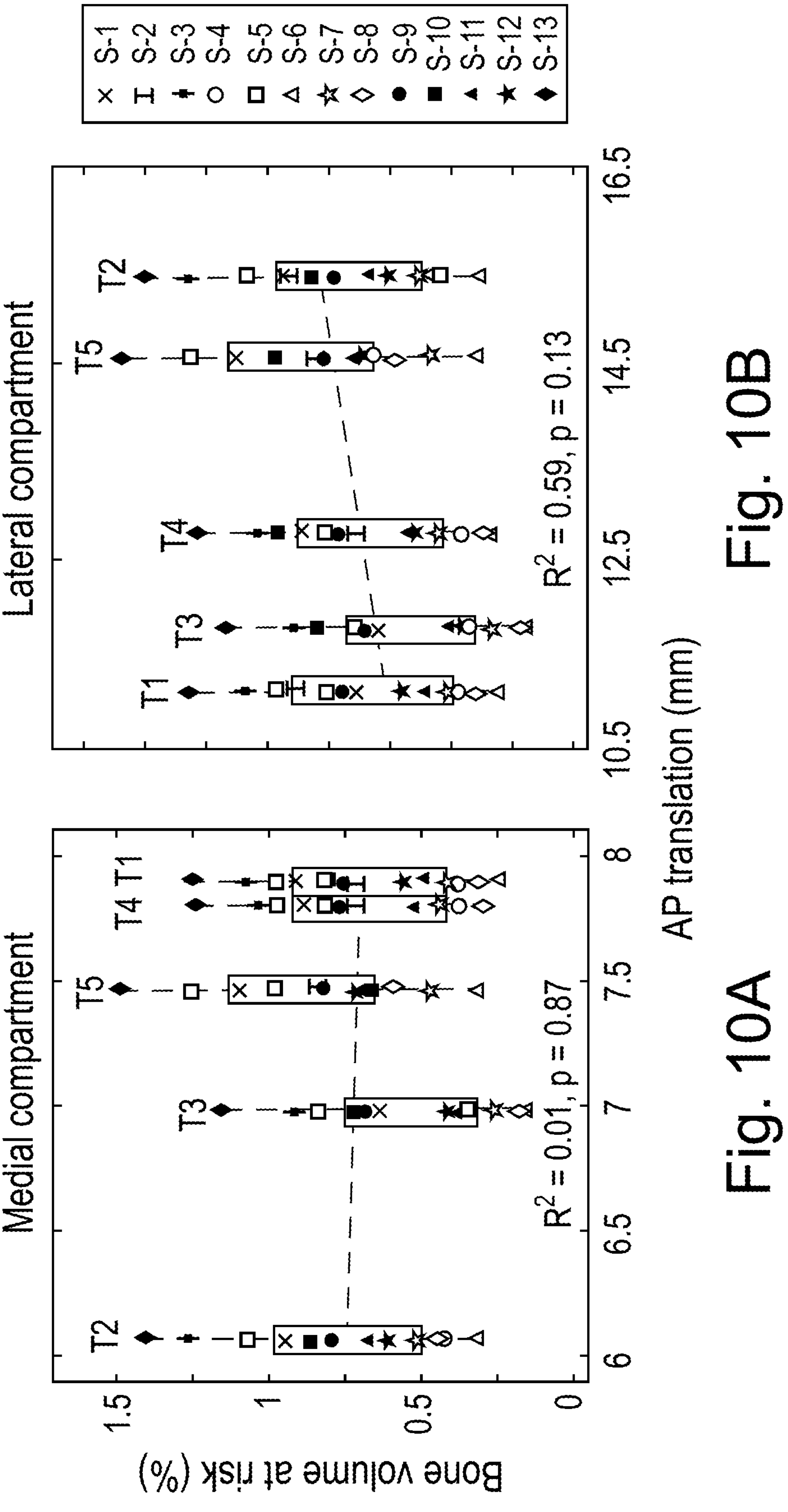
FIGS. 10A and 10B illustrate an example correlation of the maximum anterior-posterior translation for the medial compartment and lateral compartment and the composite bone volume at risk of failure during the stance phase of gait.

FIGS. 10A and 10B illustrate an example correlation of the maximum anterior-posterior (AP) translation for the medial compartment and lateral compartment and the composite bone volume at risk of failure during the stance phase of gait. The example correlation shown in FIGS. 10A and 10B is from heel strike to toe-off, for five gait trials. Each point corresponds to a given subject and gait trial. The dashed black lines represent the linear regression relationship between maximum AP translation and the composite bone volume at risk of failure.

Although the present disclosure is described by way of example herein in terms of a web-based system using web browsers, custom applications and a web site server (data processing apparatus 102), and with mobile computing devices, system 100 is not limited to that particular configuration. It is contemplated that system 100 can be arranged such that computing device 104 can communicate with, and display data received from, data processing apparatus 102 using any known communication and display method, for example, using a non-Internet browser Windows viewer coupled with a local area network protocol such as the Internetwork Packet Exchange (IPX). It is further contemplated that any suitable operating system can be used on computing device 104, for example, WINDOWS, MAC OS, OSX, LINUX, IOS, ANDROID and any suitable PDA or other computer operating system.

As used herein, the terms "function" or "module" refer to hardware, firmware, or software in combination with hardware and/or firmware for implementing features described herein. In the hardware sense, a module can be a functional hardware unit designed for use with other components or modules. For example, a module may be implemented using discrete electronic components, or it can form a portion of an entire electronic circuit such as an Application Specific Integrated Circuit (ASIC). Numerous other possibilities exist, and those of ordinary skill in the art will appreciate that the system can also be implemented as a combination of hardware and software modules. In the software sense, a module may be implemented as logic executing in a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, Perl, or Python. It will be appreciated that software modules may be callable from other modules or from themselves, and/or may be invoked in response to detected events or interrupts. Software instructions may be embedded in firmware. Moreover, the modules described herein can be implemented as software modules, but may be represented in hardware or firmware. Generally, the modules described herein refer to logical modules that may be combined with other modules or divided into sub-modules despite their physical organization or storage.

Thus, as shown and described herein, the present disclosure provides a computational framework capable of providing a holistic understanding of knee biomechanics after total knee arthroplasty. The framework provides an objective evaluation of potentially important tradeoffs between the joint level mechanics and fixation level mechanics. The framework can be utilized then to optimize implant position to maximize longevity and function of total knee replacements and generate a patient-specific presurgical plan. To this end, a workflow using a musculoskeletal model to quantify the joint level mechanics, including the tibiofemoral joint forces, are used as inputs to an finite element model to quantify the fixation level mechanics. As shown and described herein, a demonstration of the framework is provided that determines the relationship between the AP translation of the knee and both the bone-implant micromotion and the risk of bone failure.

Further, in one or more implementations the proposed framework could be applied to generating pre-surgical plans for primary and revision joint arthroplasties.

Also and as noted herein, known biomechanical studies provide detailed information regarding either the joint level mechanics or the fixation level mechanics. However, the musculoskeletal models used to predict the kinematics and loads of the tibiofemoral joint after TKA from whole body kinematics and ground reaction forces assume that the bone is rigid, which can interfere with an assessment of the bone-implant interactions. Conversely, finite element models are employed in connection with the present disclosure to assess the impact of joint loading on the bone-implant micromotion and risk of bone failure.

By combining the study of the joint level and fixation level mechanics in the integrated modeling approach of the present disclosure, an improved evaluation of the tradeoff between joint kinematics and fixation mechanics is provided.

Accordingly, the present disclosure combines the study of the joint level mechanics and the fixation level mechanics and identifies the tradeoffs between function and fixation in total knee arthroplasty. The present disclosure focuses on the relationship between joint kinematics and bone-implant interaction, and is usable to optimize fixation mechanics while maintaining proper joint mechanics (e.g., kinematics). Moreover, the workflow is applicable in the field of biomechanics of total knee arthroplasty for a wide variety of clinically relevant concerns related to how patient, surgical, and implant factors affect the function and longevity of total knee arthroplasty.

While operations shown and described herein may be in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms “a”, “an” and “the” are intended to include the plural forms as well, unless the context clearly indicates otherwise. It will be further understood that the terms “comprises” and/or “comprising”, when used in this disclosure, specify the presence of stated features, integers, steps, operations, elements, and/or components, but do not preclude the presence or addition of one or more other features, integers, steps, operations, elements, components, and/or groups thereof.

It should be noted that use of ordinal terms such as “first,” “second,” “third,” etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of “including,” “comprising,” or “having,” “containing,” “involving,” and variations thereof herein, is meant to encompass the items listed thereafter and equivalents thereof as well as additional items.

Particular embodiments of the subject matter described in this disclosure have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing can be advantageous.

What is claimed:

1. A computerized method to assess joint level biomechanics and fixation level biomechanics of joint arthroplasty devices, the method comprising:

receiving, by at least one computing device, preoperative medical information of a person requiring joint arthroplasty;

determining, by the at least one computing device as a function of at least some of the preoperative medical information of the person, at least one of bony geometries, insertion, and origin of soft tissues respectively associated with the person;

accessing, by the at least one computing device, at least one multibody rigid musculoskeletal model configured to determine at least joint level mechanics, including at least one of a bone, an implant, and soft tissue, wherein at least an aspect of the model includes a deformable body;

accessing, by the at least one computing device, information representing at least a functional activity including at least one of kinematics and ground reaction forces;

developing, by the at least one computing device using at least some of the preoperative medical information, a finite element model;

determining, by the at least one computing device as a function of at least one simulation of the multibody rigid musculoskeletal model, at least one of:

joint kinematics; and at least one of muscle, ligament, and joint contact forces;

determining, by the at least one computing device, a response of the deformable body using at least one of the determined the joint kinematics and the at least one of muscle, ligament, and joint contact forces;

integrating the multibody rigid musculoskeletal model and finite element model, by the at least one computing device applying at least one load calculated with the multibody rigid musculoskeletal model to the finite element model;

quantifying, by the at least one computing device, the bone at risk of failure as a function of a plurality simulations, including by:

quantifying, by the at least one computing device, composite micromotion as a largest value of micromotion at each implant interfacial node during each of the plurality of simulations for each of a plurality of implant interfacial nodes; and quantifying composite risk of bone failure as a largest value of the risk of bone failure at each bone element during each of the plurality of simulations at each bone element;

assessing, by the at least one computing device, the joint level biomechanics and fixation level biomechanics of joint arthroplasty devices as a function of the multibody rigid musculoskeletal model and the finite element model; and generating, by the at least one computing device, a pre-surgical plan for the person based on the information derived from the interaction between joint level biomechanics and fixation level biomechanics.

2. The method of claim 1, wherein the multibody rigid musculoskeletal model includes bones and implants represented as rigid bodies, and soft tissues represented as line elements.

3. The method of claim 1, wherein the implants are intended for total joint replacement, total knee replacement, or partial joint replacement.

4. The method of claim 3, wherein the partial joint replacement includes unicompartmental knee replacement or patellofemoral replacement.

5. The method of claim 1, wherein the soft tissues include muscle, ligament, joint capsule, or other passive structure that does not actively generate force.

6. The method of claim 1, further comprising optimizing, by the at least one computing device, ligament slack lengths of the multibody rigid musculoskeletal model to achieve a balanced knee by simulating a clinical intraoperative assessment of joint laxity.

7. The method of claim 1, wherein the multibody rigid musculoskeletal model includes at least one of a multibody dynamics model and a finite element model.

8. The method of claim 1, wherein the preoperative medical information includes imaging comprising at least one of a computerized tomography scan, magnetic resonance image, plain radiograph, and biplanar radiograph.

9. The method of claim 1, further comprising:

receiving, by the at least one computing device, demographic data associated with the person, including height and weight.

10. The method of claim 1, wherein at least some of the information representing at least one of kinematics and ground reaction forces is obtained by motion analysis techniques, fluoroscopy, wearable sensors, implantable sensors, or sensors embedded in the implant, during one or multiple representative activities of daily living.

11. The method of claim 10, wherein the at least some of the information is obtained preoperatively on the person requiring joint arthroplasty.

12. The method of claim 1, wherein the kinematics and ground reaction forces are determined from a library of kinematics and ground reaction forces on healthy individuals or individuals having received the same joint replacement as the person by selecting at least one of the healthy individuals or individuals having received the same joint replacement as the person, wherein the selected at least one individual has characteristics similar to the person.

13. The method of claim 1, wherein the pre-surgical plan includes a choice of position and rotation of the implant with respect to anatomic landmarks and the design of the implant, including constraint and type of fixation.

14. The method of claim 1, further comprising-:

determining, by the at least one computing device, joint level kinematics from whole body kinematics using inverse kinematics; and/or determining, by the at least one computing device, joint level kinematics, joint forces, ligament forces, and muscle forces using a dynamic simulation.

15. The method of claim 1, further comprising:

scaling and aligning, by the at least one computing device, segments of the multibody rigid musculoskeletal model.

16. The method of claim 1, further comprising:

improving, as a function of information using the joint level mechanics and the interface level mechanics, the choice of implant design and position to maximize at least one of implant longevity and function.

17. The method of claim 1, wherein determining the bone at risk of failure further comprises:

dividing, by the at least one computing device, a value representing a volume of bone with strains greater than yield by a value representing a volume of interfacial bone.

18. The method of claim 1, wherein quantifying composite micromotion further comprises:

determining, by the at least one computing device, a largest value of micromotion at each of the plurality of implant interfacial nodes during the plurality of simulations.

19. The method of claim 1, wherein quantifying composite risk of bone failure at each bone element further comprises:

determining, by the at least one computing device, a largest value of the risk of bone failure at each bone element during the plurality of simulations.

20. The method of claim 1, wherein assessing the fixation level biomechanics includes at least one of: stress shielding, cement mantle failure, cement-bone debonding, and implant-cement debonding.

21. The method of claim 1, further comprising:

identifying in the multibody rigid musculoskeletal model, by the at least one computing device, implant interfacial nodes of an insert's articular surface that experience load during a stance phase of gait; and extracting, by the at least one computing device, a location and profile of force components of each of the implant interfacial nodes.

22. A computerized system to assess joint level biomechanics and fixation level biomechanics of joint arthroplasty devices, the system comprising:

at least one computing device, configured by executing instructions stored on non-transitory processor readable media to perform steps including:

receiving preoperative medical information of a person requiring joint arthroplasty;

determining, as a function of at least some of the preoperative medical information of the person, at least one of bony geometries, insertion, and origin of soft tissues respectively associated with the person;

accessing at least one musculoskeletal model including at least one multibody rigid musculoskeletal model configured to determine at least joint level mechanics including at least one of a bone, an implant, and soft tissue, wherein at least an aspect of the model includes a deformable body;

accessing information representing at least a functional activity including at least one of kinematics and ground reaction forces;

developing, by the at least one computing device using at least some of the preoperative medical information, a finite element model;

determining, as a function of at least one simulation of the multibody rigid musculoskeletal model, at least one of:

joint kinematics; and at least one of muscle, ligament, and joint contact forces;

determining a response of the deformable body using at least one of the determined the joint kinematics and the at least one of muscle, ligament, and joint contact forces;

integrating the multibody rigid musculoskeletal model and finite element model, by applying at least one load calculated with the multibody rigid musculoskeletal model to the finite element model;

quantifying the bone at risk of failure as a function of a plurality simulations, including by:

quantifying composite micromotion as a largest value of micromotion at each implant interfacial node during each of the plurality of simulations for each of a plurality of implant interfacial nodes; and quantifying composite risk of bone failure as a largest value of the risk of bone failure at each bone element during each of the plurality of simulations at each bone element;

assessing the joint level biomechanics and fixation level biomechanics of joint arthroplasty devices, as a function of the multibody rigid musculoskeletal model and the finite element model; and generating, a pre-surgical plan for the person based on the information derived from the interaction between joint level biomechanics and fixation level biomechanics.

* * * * *